United States Patent
Shindo

(10) Patent No.: US 8,128,286 B2
(45) Date of Patent: Mar. 6, 2012

(54) X-RAY CT APPARATUS

(75) Inventor: Yasutaka Shindo, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 116 days.

(21) Appl. No.: 12/558,194

(22) Filed: Sep. 11, 2009

(65) Prior Publication Data
US 2010/0067652 A1    Mar. 18, 2010

(30) Foreign Application Priority Data
Sep. 12, 2008 (JP) ................. P2008-235027

(51) Int. Cl.
*H05G 1/02* (2006.01)
*G01N 23/083* (2006.01)
(52) U.S. Cl. .............. 378/197; 378/193; 378/4
(58) Field of Classification Search .......... 378/4, 17, 378/193, 197, 204, 210
See application file for complete search history.

(56) References Cited

U.S. PATENT DOCUMENTS

| 4,750,195 A * | 6/1988 | Takahashi ............ 378/15 |
| 4,928,292 A * | 5/1990 | Zupancic et al. ........ 378/17 |
| 5,042,162 A * | 8/1991 | Helms ................ 33/503 |
| 2002/0168044 A1 * | 11/2002 | Tybinkowski et al. ........ 378/4 |
| 2006/0202650 A1 * | 9/2006 | Hausner et al. ........... 318/268 |

FOREIGN PATENT DOCUMENTS

| CN | 101069644 A | 11/2007 |
| JP | 2-200251 | 8/1990 |
| JP | 2002-172112 | 6/2002 |

OTHER PUBLICATIONS

Office Action issued Feb. 22, 2011, in Chinese Patent Application No. 200910169170.1 (with partial English translation).

\* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

An X-ray CT apparatus includes: a base; a main frame including a pair of tilt shafts, the main frame being supported in a tiltable manner by the base with a pair of bearings interposed in between, the bearings configured to rotatably support the respective tilt shafts; an X-ray tube and an X-ray detector positioned to face each other; an annular rotor configured to hold the X-ray tube and the X-ray detector, the rotor rotatably supported by the main frame with a bearing interposed in between; and a pair of reinforcement members extended from the main frame. One end of each of the pair of tilt shafts is fixed to the main frame, and the other end of each of the pair of tilt shafts is fixed to the respective reinforcement members.

3 Claims, 3 Drawing Sheets

X-RAY CT APPARATUS

CROSS REFERENCE OF THE RELATED APPLICATION

This application is based on and claims the benefit of priority from Japanese Patent Application No. 2008-235027, filed on Sep. 12, 2008; the entire contents of which are incorporated herein by reference.

BACKGROUND OF THE INVENTION

1. Field of the Invention

The present invention relates to an X-ray CT apparatus, and particularly to an X-ray CT apparatus configured to take an X-ray CT scan while rotating an annular rotor holding an X-ray tube and an X-ray detector.

2. Description of the Related Art

As described in JP-A No. 2002-172112 (KOKAI), for instance, there has been known an X-ray CT apparatus including an annular rotor which holds an X-ray tube and an X-ray detector, and which is rotatably supported by a stator with a bearing interposed therebetween. The diameter of the bearing rotatably supporting the rotor is set almost equal to the diameter of a diagnosis opening portion which is formed inside the rotor. This X-ray CT apparatus takes an X-ray CT scan of a subject by: positioning the subject inside the diagnosis opening portion; subsequently emitting X-rays onto the subject from the X-ray tube while rotating the rotor around the subject; and detecting the X-rays transmitted through the subject by the X-ray detector.

Furthermore, as described in JP-A No. Hei 02-200251 (KOKAI), there has been known an X-ray CT apparatus which includes a tilt mechanism configured to tilt its rotor at a desired tilt angle. The X-ray CT apparatus including the tilt mechanism is capable of taking X-ray CT scans of a subject at various angles by tilting the rotor at desired tilt angles by use of the tilt mechanism.

In the foregoing X-ray CT apparatuses, however, no considerations have been given to the following points.

In these years, a rotational speed of a rotor tends to be increased because of a demand to shorten a time required to take an X-ray CT scan of a subject. When a rotor is rotated at a higher rotational speed, the rotor is distorted due to a slight displacement between the rotation center and the gravity center of the rotor, and thus the rotor vibrates in rotation. The vibration of the rotor in rotation puts an X-ray CT scan plane out of position, and thus deteriorates the quality of an image obtained by taking an X-ray CT scan.

Other causes of the vibration of the rotor in rotation include such phenomena that: a base portion of the cantilevered tilt shaft supporting the rotor in a tiltable manner is deformed; the rotor is unevenly supported between its two sides because a drive cylinder configured to tilt the rotor is provided at only one side of the rotor; a base fixed to the floor to support the rotor resonates with the rotation of the rotor.

SUMMARY OF THE INVENTION

An object of the present invention is to provide an X-ray CT apparatus capable of suppressing vibration of a rotor even while rotating the rotor at high speed, and thus enhancing the quality of an image obtained by taking an X-ray CT scan.

A first aspect of the present invention is an X-ray CT apparatus includes: a base; a main frame including a pair of tilt shafts, the main frame being supported in a tiltable manner by the base with a pair of bearings interposed in between, the bearings configured to rotatably support the respective tilt shafts; an X-ray tube and an X-ray detector positioned to face each other; an annular rotor configured to hold the X-ray tube and the X-ray detector, the rotor rotatably supported by the main frame with a bearing interposed in between; and a pair of reinforcement members extended from the main frame. One ends of the pair of tilt shafts are fixed to the main frame, and the other ends of the pair of tilt shafts are fixed to the respective reinforcement members.

A second aspect of the present invention is an X-ray CT apparatus includes: a base; a main frame including a pair of tilt shafts, the main frame being supported in a tiltable manner by the base with a pair of bearings interposed in between, the bearings configured to rotatably support the respective tilt shafts; an X-ray tube and an X-ray detector positioned to face each other; an annular rotor configured to hold the X-ray tube and the X-ray detector, the rotor rotatably supported by the main frame with a bearing interposed in between; an expandable and contractible drive cylinder placed at a side of one of the pair of tilt shafts, the drive cylinder having one end connected to the base, and the other end connected to the main frame, the drive cylinder including an expansion/contraction driver which is a drive source for expansion and contraction; and an expandable and contractible cylinder placed at a side of the other one of the pair of tilt shafts, the cylinder having one end connected to the base, and the other end connected to the main frame, the cylinder including a brake configured to restrain expansion and contraction.

A third aspect of the present invention is an X-ray CT apparatus includes: a base; a main frame including a pair of tilt shafts, the main frame being supported in a tiltable manner by the base with a pair of bearings interposed in between, the bearings configured to rotatably support the respective tilt shafts; an X-ray tube and an X-ray detector positioned to face each other; an annular rotor configured to hold the X-ray tube and the X-ray detector, the rotor rotatably supported by the main frame with a bearing interposed in between; and supporters located across the rotor, the supporters configured to connect the base and the main frame. The base is fixed in intimate contact with a floor surface at positions where any node of a secondary vibration and any node of a tertiary vibration do not overlap each other, the secondary and tertiary vibrations occurring in the base between two endmost fixation positions where the base is fixed to the floor surface.

DESCRIPTION OF THE PREFERRED EMBODIMENTS

Figure 1:
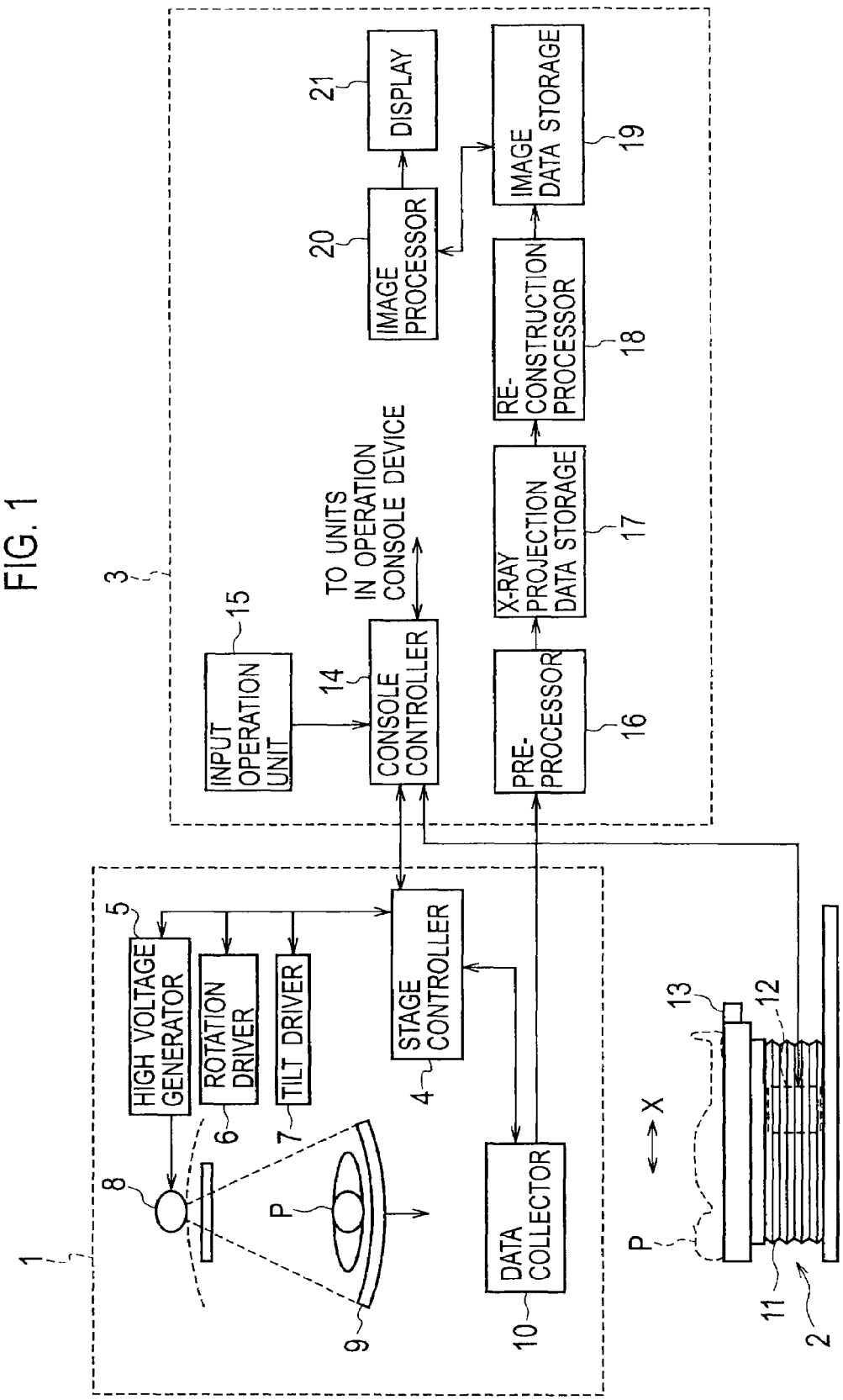
FIG. 1 is a block diagram showing a schematic configuration of an X-ray CT apparatus according to an embodiment of the present invention.

Referring to the drawings, descriptions will be hereinbelow provided for an embodiment of the present invention.

FIG. 1 is a block diagram showing a schematic configuration of an X-ray CT apparatus according to the embodiment of the present invention. The X-ray CT apparatus includes a stage device 1, a bed device 2 and an operation console device 3.

The stage device 1 includes a stage controller 4, a high voltage generator 5, a rotation driver 6, a tilt driver 7, an X-ray tube 8, an X-ray detector 9 and a data collector 10.

The bed device 2 includes a bed base 11, a bed driver 12 and a bed top board 13.

The operation console device 3 includes a console controller 14, an input operation unit 15, a pre-processor 16, an X-ray projection data storage 17, a reconstruction processor 18, an image data storage 19, an image processor 20 and a display 21.

The stage controller 4 controls all the component parts in the stage device 1 in response to inputs from the input operation unit 15 of the operation console device 3.

The high voltage generator 5 supplies the X-ray tube 8 with a high voltage needed for the X-ray tube 8 to emit X-rays in accordance with a control signal transmitted from the stage controller 4.

The X-ray tube 8 emits X-rays by using the high voltage supplied from the high voltage generator 5. The X-rays emitted from the X-ray tube 8 is shaped like a fan or a cone.

The X-ray detector 9 detects the X-rays which are emitted from the X-ray tube 8 and subsequently transmit through a subject P. In a case of a single-slice CT apparatus, the X-ray detector 9 includes, for instance, 1000 channels of X-ray detecting elements which are arrayed in a line forming a fan or a straight line. In a case of a multiple-slice CT apparatus, the X-ray detector 9 is constructed as a two-dimensional X-ray detector including X-ray detecting elements which are aligned in an array in two directions (a slice direction and a channel direction) orthogonal to each other.

The data collector 10 includes data collecting elements which are aligned in an array as similar to the X-ray detecting elements of the X-ray detector 9. The data collector 10 collects the X-rays (actually, detection signals) detected by the X-ray detector 9 in accordance with a data collection control signal outputted from the stage controller 4. The data thus collected constitutes X-ray projection data.

The rotation driver 6 drives a motor (not illustrated) in accordance with a control signal outputted from the stage controller 4, and rotationally drives a rotor described later.

The tilt driver 7 expands and contracts a drive cylinder and a following cylinder described later, in accordance with a control signal outputted from the stage controller 4, and tilts the rotor together with a main frame described later, at a desired angle.

In accordance with an input received from the input operation unit 15 of the operation console device 3, the bed driver 12 moves the bed base 11 upward and downward, and moves the bed top board 13 in longitudinal directions (directions indicated by an arrow X). The subject P who undergoes an X-ray CT scan is placed on the bed top board 13 in such a direction that the body axis of the subject P and the movement directions (the directions indicated by the arrow X) of the bed top board 13 coincide with each other.

The input operation unit 15 includes a keyboard, a touch panel, a mouse, and the like. Various input operations for driving the X-ray CT apparatus are carried out through the input operation unit 15.

The console controller 14 generates a control signal in accordance with an input received from the input operation unit 15. The console controller 14 transmits this control signal to the stage controller 4, the bed driver 12 and the component parts in the operation console device 3.

The pre-processor 16 applies preprocessing, such as a sensitivity correction and an X-ray strength correction, to the X-ray projection data outputted from the data collector 10. The X-ray projection data to which the preprocessing such as the sensitivity correction are applied by the pre-processor 16 is temporarily stored in the X-ray projection data storage 17.

The reconstruction processor 18 applies a back projection processing to the X-ray projection data which is stored in the X-ray projection data storage 17, and thereby reconstructs the image data. A method adopted for this back projection is the same as publicly-known methods, thereby description thereof is omitted. In addition, in a case where the reconstruction processor 18 applies an interpolation processing to the X-ray projection data, the reconstruction processor 18 acquires X-ray projection data of an object slice position by use of any one of publicly known interpolation methods such as the 360-degree interpolation method, the 180-degree interpolation method (the opposed data interpolation method), and the like.

The image data thus reconstructed is temporarily stored in the image data storage 19, and is thereafter sent to the image processor 20. In accordance with an input received from the input operation unit 15, the image processor 20 converts, by using a publicly-known method, the image data to image data such as: a cross-sectional image of a desired cross-section: a projection image made in a desired direction; or a three-dimensional image formed by use of a rendering process. Subsequently, the image processor 20 sends the image data to the display 21. The display 21 displays an image on the basis of the image data.

Figure 2:
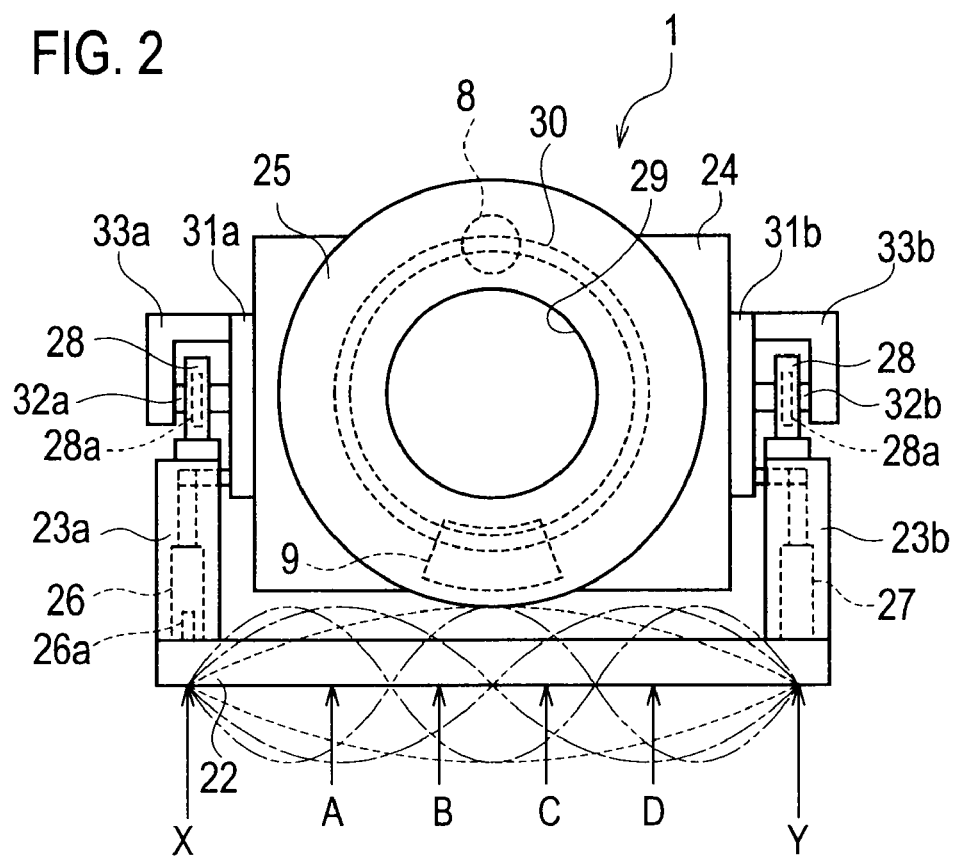
FIG. 2 is a front view showing an external configuration of a stage unit.
Figure 3:
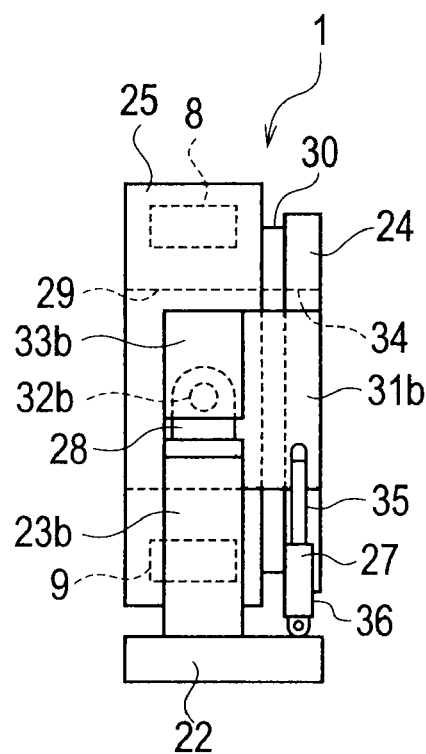
FIG. 3 is a side view showing the external configuration of a stage.

FIG. 2 is a front view showing an external configuration of the stage device 1. FIG. 3 is a side view showing the external configuration of the stage device 1.

The stage device 1 includes: a base 22; a pair of support bars 23a, 23b which are supporting members; a main frame 24; a rotor 25; a drive cylinder 26; and a following cylinder 27.

The base 22 is shaped like a rectangular frame. The support bars 23a, 23b are installed upright on the base 22, i.e., at positions that are in both end portions in a longitudinal direction of the base 22, and are in substantially central portions in a shorter side direction of the base 22. A pillow block 28 is fixed to the top end portion of each of the support bars 23a, 23b. The pillow block 28 is a shaft box which contains a bearing 28a in its inside. A portion of the pillow block 28 supporting an outer ring of the bearing 28a is formed into a shape curving concavely. The bearing 28a is supported inside the pillow block so as to be capable of being eccentric.

The rotor 25 has a diagnosis opening portion 29 formed in the center portion. The X-ray tube 8 and the X-ray detector 9 are held in their respective positions so as to face each other with this diagnosis opening portion 29 interposed in between. The diagnosis opening portion 29 is a part which the subject P undergoing the X-ray CT scan is put into or taken out of. By sliding the bed top board 13 in the horizontal directions, the subject P placed on the bed top board 13 is put into or taken out of the diagnosis opening portion 29.

The rotor 25 is rotatably supported by the main frame 24 with a bearing 30 interposed in between, and is rotatable about the diagnosis opening portion 29. The bearing 30 is located on a circle having radius equal to a rotation locus of the X-ray tube 8 that rotates with the rotation of the rotor 25, and is located behind the X-ray tube 8 and the X-ray detector 9, that is, on the opposite side of the X-ray tube 8 and the X-ray detector 9 from the bed device 2.

The main frame 24 is attached onto the base 22 with the pair of support bars 23a, 23b interposed in between. The rotor 25 is rotatably supported by the main frame 24 with the bearing 30 interposed in between. Arms 31a, 31b are fixed to the two sides of the main frame 24 with the rotor 25 interposed therebetween. These arms 31a, 31b extend toward the sides of the rotor 25. One end of one tilt shaft 32a is fixed to the one arm 31a, whereas one end of the other tilt shaft 32b is fixed to the other arm 31b. The tilt shafts 32a, 32b extend in the respective horizontal directions which are orthogonal to the rotation center of the rotor 25. The tilt shafts 32a, 32b are rotatably supported by the bearings 28a accommodated in the pillow blocks 28, respectively.

In addition, one end of an L-shaped reinforcement bracket 33a being a reinforcement member is fixed to the arm 31a, whereas one end of an L-shaped reinforcement bracket 33b being a reinforcement member is fixed to the arm 31b. The other end of the reinforcement bracket 33a is fixed to the other end of the tilt shaft 32a, whereas the other end of the reinforcement bracket 33b is fixed to the other end of the tilt shaft 32b. Because these reinforcement brackets 33a, 33b are provided, the two ends of the tilt shaft 32a are supported by the arm 31a and the reinforcement bracket 33a, respectively, whereas the two ends of the tilt shaft 32b are supported by the arm 31b and the reinforcement bracket 33b, respectively.

In addition, in the center portion of the main frame 24, an opening portion 34 whose diameter is almost equal to the diameter of the diagnosis opening portion 29 of the rotor 25 is formed right behind the diagnosis opening portion 29.

The drive cylinder 26 is placed on a side corresponding to the one tilt shaft 32a. One end of the drive cylinder 26 is swingably connected to the base 22, whereas the other end is swingably connected to the arm 31a. The drive cylinder 26 includes an electric motor 26a which is an expansion/contraction driver. When this electric motor 26a is driven by the tilt driver 7, the drive cylinder 26 expands and contracts.

Figure 4:
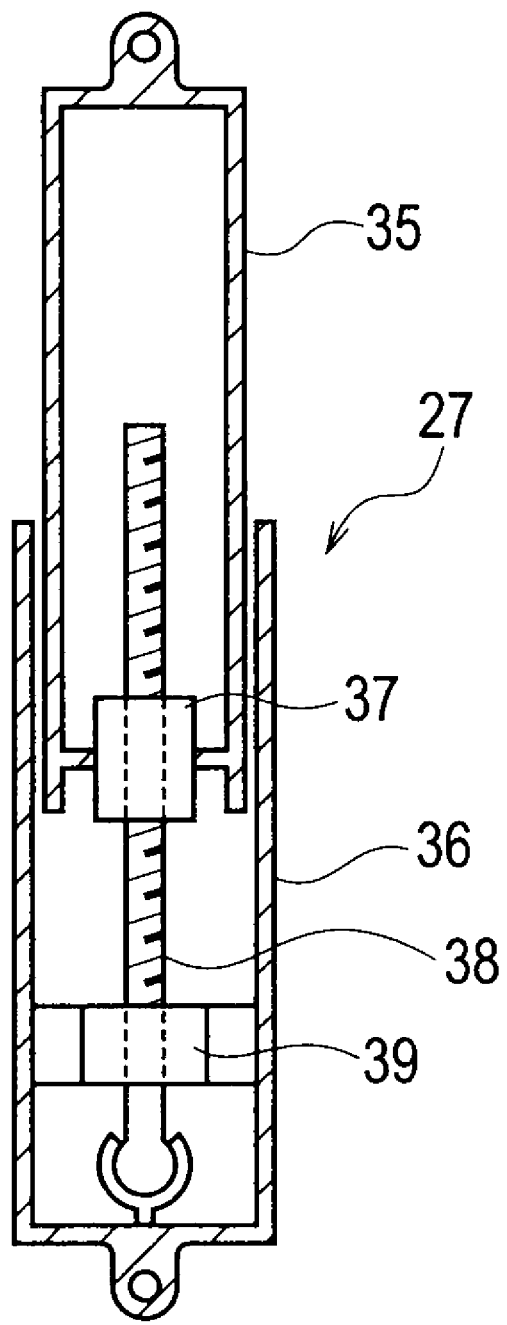
FIG. 4 is a longitudinal sectional front view showing a following cylinder.

The following cylinder 27 is placed on a side corresponding to the other tilt shaft 32b. One end of the following cylinder 27 is swingably connected to the base 22, whereas the other end is swingably connected to the arm 31b. As shown in FIG. 4, the following cylinder 27 includes a first pipe 35 and a second pipe 36. The first pipe 35 is slidably fitted into the second pipe 36. The first pipe 35 is connected to the arm 31b, whereas the second pipe 36 is connected to the base 22. A nut 37 is fixed inside the first pipe 35, and an end of a screw stock 38 is rotatably held inside the second pipe 36. The screw stock 38 is screwed into the nut 37. This following cylinder 27 is configured to expand or contract in a way that the screw stock 38 having screwed in the nut 37 rotates on its axis when an external force acts on the first pipe 35 or the second pipe 36 in an expanding or contracting direction. Furthermore, a solenoid brake 39 configured to restrain the rotation of the screw stock 38 when the electricity is cut off is provided inside the second pipe 36. The restraint of the rotation of the screw stock 38 by the brake 39 restrains the expansion and contraction of the following cylinder 27. The ON and OFF control of the solenoid brake 39 is carried out in linkage with the control of the tilt driver 7 for causing the drive cylinder 26 to expand and contract.

The base 22 is fixed to the floor surface on which the stage device 1 is placed by use of anchor bolts. In FIG. 2, a wave line indicated by a broken line represents a primary vibration of the base 22 which is generated between the two endmost fixation positions X, Y where the base 22 is fixed to the floor surface; a wave line indicated by a long dashed short dashed line represents a secondary vibration of the base 22 which is generated between the fixation positions X, Y; and a wave line indicated by a long dashed double-short dashed line represents a tertiary vibration of the base 22 which is generated between the fixation positions X, Y. Between the fixation positions X, Y, the base 22 is fixed to the floor surface at four fixation positions A, B, C, D. These fixation positions A, B, C, D are determined so that the secondary and tertiary vibrations which occur in the base 22 between the fixation positions X, Y do not overlap each other at any node. Specifically, the position A is a position which is away from the position X by a quarter of the distance between the positions X, Y; the position B is a position which is away from the position X by five-twelfths of the distance between the positions X, Y; the position C is a position which is away from the position X by seven-twelfths of the distance between the positions X, Y; and the position D is a position which is away from the position X by three-fourths of the distance between the positions X, Y.

When an X-ray CT scan is taken of the subject P by use of the X-ray CT apparatus having such configuration, the subject P placed on the bed top board 13 is positioned inside the diagnosis opening portion 29, and X-rays are emitted from the X-ray tube 8 while the rotor 25 is rotated. In addition, the drive cylinder 26 is expanded or contracted depending on the necessity, and the rotor 25 together with the main frame 24 is thus tilted about the tilt shafts 32a, 32b.

The rotor 25 is rotatably supported by the main frame 24 with the bearing 30 interposed in between. As the rotational speed of the rotor 25 increases, the rotor 25 is easier to vibrate. However, in this X-ray CT apparatus, the bearing 30 is located on the circle having radius equal to the rotation locus of the X-ray tube 8 that rotates with the rotation of the rotor 25, and is larger in diameter than a bearing according to a conventional example whose diameter is a dimension almost equal to the diameter of the diagnosis opening portion 29. The larger diameter of the bearing 30 makes it possible to restrain the distortion of the rotor 25 in rotation, and accordingly to restrain the vibration of the rotor 25 which occurs due to this distortion.

Thereby, in the X-ray CT scan taken while rotating the rotor 25, the X-ray CT scan plane is less likely to be out of position. Accordingly, the quality of the image obtained by taking the X-ray CT scan can be enhanced.

When changing the direction in which the X-ray CT scan is applied to the subject P, the rotor 25 together with the main frame 24 is tilted about the axes of the respective tilt shafts 32a, 32b. The tilt shafts 32a, 32b are supported by their two ends, respectively, in a way that the one end of each of the tilt shafts 32a, 32b are fixed to the corresponding one of arms 31a, 31b whereas the other end of each of the tilt shafts 32a, 32b are fixed to the corresponding one of reinforcement brackets 33a, 33b. For this reason, it is possible to enhance the rigidities of the respective tilt shafts 32a, 32b without making the tilt shaft 32a, 32b thicker. As a result, the deformations of the base portions of the tilt shafts 32a, 32b connected to the arms 31a, 31b are prevented, and concurrently the tilt shafts 32a, 32b is prevented from tilting with respect to the arms 31a, 31b, respectively. Accordingly, it is possible to prevent the rotor 25 and the main frame 24 from vibrating due to the tilts of the tilt shafts 32a, 32b with respect to the arms 31a, 31b.

Thereby, in the X-ray CT scan taken while rotating the rotor 25, the X-ray CT scan plane is less likely to be out of position. Accordingly, the quality of the image obtained by taking the X-ray CT scan can be enhanced.

In the present embodiment, the pillow blocks 28 are used to rotatably support the respective tilt shafts 32a, 32b. Here, a portion of each pillow block 28 configured to support the outer ring of the corresponding bearing 28a is formed into a concave curved shape. By using these pillow blocks 28, the main frame 24 can be supported in a tiltable manner, even in a case where the two pillow blocks 28 are attached to their respective positions with poor accuracy, or where the two tilt shafts 32a, 32b are attached to their respective positions with poor accuracy.

Instead of these pillow blocks 28, shaft boxes including deep grooves may be attached to the upper portions of the support bars 23a, 23b so that the outer ring of the bearings 28a configured to rotatably support the respective tilt shafts 32a, 32b are fitted into the deep grooves, respectively. When the bearings 28a configured to rotatably support the tilt shafts 32a, 32b are installed in the shaft boxes including such deep grooves, it is possible to prevent the tilt shafts 32a, 32b from tilting with respect to the arms 31a, 31b, respectively. Accordingly, it is possible to prevent the rotor 25 and the main frame 24 from vibrating due to the tilts of the tilt shafts 32a, 32b with respect to the arms 31a, 31b.

When the rotor 25 is tilted together with the main frame 24, the drive cylinder 26 provided near the tilt shaft 32a on one side is expanded or contracted. Thereby, the rotor 25 together with the main frame 24 is tilted about the tilt shafts 32a, 32b. In a case where the drive cylinder 26 is expanded or contracted, the brake 39 of the following cylinder 27 near the tilt shaft 32b on the other side is turned off, and the following cylinder 27 is expanded or contracted in conjunction with the expansion or contraction of the drive cylinder 26. Once the expansion or contraction of the drive cylinder 26 is completed, the brake 39 of the following cylinder 27 is turned on, and the expansion and contraction of the following cylinder 27 is restrained.

Because the drive cylinder 26 is provided near the tilt shaft 32a on the one side and the following shaft 27 is provided near the tilt shaft 32b on the other side in this manner, the rotor 25 and the main frame 24 are evenly supported at the two sides of the rotor 25. This makes it possible to prevent the vibrations of the rotor 25 and the main frame 24 during the rotation of the rotor 25, although the vibrations would otherwise occur due to uneven support of the rotor 25 and the main frame 24 between the two sides of the rotor 25.

Thereby, in the X-ray CT scan taken while rotating the rotor 25, the X-ray CT scan plane is less likely to be out of position. Accordingly, the quality of the image obtained by taking the X-ray CT scan can be enhanced.

The base 22 is fixed to the floor surface on which the stage device 1 is placed by use of the anchor bolts. The base 22 is fixed to the floor surface at such positions that the secondary and tertiary vibrations of the base 22 which occur between the fixation positions X, Y do not overlap each other at any node, the fixation positions X, Y being two endmost positions where the base 22 is fixed to the floor surface. Thus, the vibration of the base 22 during the rotation of the rotor 25 can be restrained. Accordingly, the rotor 25 and the main frame 24 can be prevented from vibrating due to the vibration of the base 22.

Thereby, in the X-ray CT scan taken while rotating the rotor 25, the X-ray CT scan plane is less likely to be out of position. Accordingly, the quality of the image obtained by taking the X-ray CT scan can be enhanced.

Note that, in the foregoing embodiment, the drive cylinder 26 and the following cylinder 27 are used together. However, the present invention is not limited to this. For instance, instead of the following cylinder 27, a different drive cylinder may be used. Here, the different drive cylinder and the drive cylinder 26 expand and contract in synchronism with each other.

The embodiment of the present invention has been described above. However the descriptions only exemplify the concrete example, and do not limit the invention. The concrete configurations and the like of each component parts can be modified whenever deemed necessary. In addition, the operations/working-effects described in the embodiment are only those enumerated as most preferable operations/working-effects brought about by the present invention. The operations/working-effects of the present invention are not limited to those described in the embodiment of the present invention.

What is claimed is:

1. An X-ray CT apparatus comprising:
 a base;
 a main frame including a pair of tilt shafts, the main frame being supported in a tiltable manner by the base with a pair of first bearings interposed in between, the first bearings configured to rotatably support the respective tilt shafts;
 an X-ray tube and an X-ray detector positioned to face each other;
 an annular rotor configured to hold the X-ray tube and the X-ray detector, the rotor rotatably supported by the main frame with a second hearing interposed in between, the second bearing being located on a circle having a radius approximately equal to a rotation locus of the center of the X-ray tube that rotates with the rotation of the rotor; and
 a pair of reinforcement members extended from the main frame,
 wherein one of each of the pair of tilt shafts is fixed to the main frame, and the other of each of the pair of tilt shafts is fixed to the respective reinforcement members.

2. An X-ray CT apparatus comprising:
 a base;
 a main frame including a pair of tilt shafts, the main frame being supported in a tiltable manner by the base with a pair of first bearings interposed in between, the first bearings configured to rotatably support the respective tilt shafts;
 an X-ray tube and an X-ray detector positioned to face each other;
 an annular rotor configured to hold the X-ray tube and the X-ray detector, the rotor rotatably supported by the main frame with a second bearing interposed in between, the second bearing being located on a circle having a radius approximately equal to a rotation locus of the center of the X-ray tube that rotates with the rotation of the rotor;
 an expandable and contractible drive cylinder placed at a side of one of the pair of tilt shafts, the drive cylinder having one end connected to the base, and the other end connected to the main frame, the drive cylinder including an expansion/contraction driver which is a drive source for expansion and contraction; and
 an expandable and contractible cylinder placed at a side of the other one of the pair of tilt shafts, the cylinder having one end connected to the base, and the other end connected to the main frame, the cylinder including a brake configured to restrain expansion and contraction.

3. An X-ray CT apparatus comprising:
 a base;
 a main frame including a pair of tilt shafts, the main frame being supported in a tiltable manner by the base with a pair of first bearings interposed in between, the first bearings configured to rotatably support the respective tilt shafts;
 an X-ray tube and an X-ray detector positioned to face each other;
 an annular rotor configured to hold the X-ray tube and the X-ray detector, the rotor rotatably supported by the main frame with a second bearing interposed in between, the second bearing being located on a circle having a radius approximately equal to a rotation locus of the X-ray tube that rotates with the rotation of the rotor; and supporters located across the rotor, the supporters configured to connect the base and the main frame, wherein the base is fixed in intimate contact with a floor surface at positions where, for primary, secondary and tertiary vibrations of the base, any node of the secondary vibration of the base and any node of the tertiary vibration of the base do not overlap each other, the secondary and tertiary vibrations occurring in the base between two endmost fixation positions where the base is fixed to the floor surface.

* * * * *